(12) United States Patent
Leung et al.

(10) Patent No.: US 7,550,281 B2
(45) Date of Patent: Jun. 23, 2009

(54) METHOD FOR PRODUCTION OF ALPHA-AMYLASE IN RECOMBINANT BACILLUS

(75) Inventors: Yun Chung Leung, Kowloon (HK); Wai Hung Lo, Kowloon (HK); Jeffery Errington, Oxford (GB)

(73) Assignee: The Hong Kong Polytechnic University, Kowloon (HK)

( * ) Notice: Subject to any disclaimer, the term of this patent is extended or adjusted under 35 U.S.C. 154(b) by 203 days.

(21) Appl. No.: 10/212,806

(22) Filed: Aug. 7, 2002

(65) Prior Publication Data

US 2002/0187541 A1 Dec. 12, 2002

Related U.S. Application Data

(62) Division of application No. 09/684,337, filed on Oct. 10, 2000, now abandoned.

(51) Int. Cl.
*C12N 9/28* (2006.01)
*C12N 15/75* (2006.01)
*C12N 1/21* (2006.01)

(52) U.S. Cl. ............... 435/202; 435/320.1; 435/252.31

(58) Field of Classification Search .............. 435/4, 435/6, 69.1, 183, 200, 252.3, 252.5, 320.1, 435/202, 320, 252.31; 536/23.2, 23.5
See application file for complete search history.

(56) References Cited

U.S. PATENT DOCUMENTS 4,610,964 A * 9/1986 Lompe ............... 435/202

OTHER PUBLICATIONS

Yuko Yoneda, "Increased Production of Extracellular Enzymes by the Synergistic Effect of Genes Introduced into *Bacillus substilis* by Stepwise Transformation", Applied and Environmental Microbiology, 39:274-276 (1980).

Leung et al., "Characterization of an insertion in the Phase φ105 genome that blocks host *Bacillus subtilis* lysis and provides strong expression of heterologous genes", Gene, 154:1-6 (1995).

Thornewell et al., "An efficient expression and secretion system based on *Bacillus* subtiis phage φ105 and its use for the production of *B. cereus* β-lactamas I", Gene, 133:47-53 (1993).

Wei et al., "Plasmid Stability and α-Amylase Production in Batch and continuous Cultures of *Bacillus subtilis* TN106[Pat5]", 33:1010-1020 (1989).

Jeff Errington, "Gene Cloning and Expression Vectors Based on *Bacillus subtilis* Bacteriophage φ105", Microbiology Unit Department of Biochemistry, Univ. of Oxford, pp. 217-227.

Park et al., "Enhanced α-Amylase Production in Recombinant *Bacillus brevis* by Fed-Batch Culture with Amino Acid Control", Biotechnology and Bioengineering, 49:26-44 (1996).

Anagnostopoulos et al., "Requirements for Transformation in *Bacillus subtilis*", Department of Microbiology, School of Medicine, Western Reserve University, 81:741-746 (1961).

Suzuki et al., "Mass production of thiostrepton by fed-batch culture of *Streptomyces laurentii* with pH-stat modal feeding of multi-substrate", Appl. Microbiol. Biotechnol. 25:526-531 (1987).

Jeong et al., "High-Level Production of Human Leptin by Fed-Batch Cultivation of Recombinant *Escherichia coli* and its Purification", Applied and Environmental Microbiology, 65:3027-3032 (1999).

Steyn et al., "Co-expression of a *Saccharomyces diastaticus* glucoamylase-encoding gene and a *Bacillus amyloliquefaciens* alpha-amylase-encoding gene in *Saccharamyces cerevisiae*", National Library of Medicine, Pub Med, Abstract of Gene, 100:85-93 (1991).

Emori et al., J. Bacteriol., 1990, vol. 172(9):4901-4908.
Leung et al., Gene, 1995, vol. 154:1-6.

* cited by examiner

*Primary Examiner*—Rebecca E. Prouty
(74) *Attorney, Agent, or Firm*—Leydig, Voit & Mayer, Ltd.

(57) ABSTRACT

Disclosed is a novel recombinant Bacillus bacterial strain constructed by genetic engineering which has high productivity of aipha-amylase. The Bacillus strain comprises an alpha-amylase gene inserted in the Bacillus chromosome under transcriptional control of a phage promoter. An efficient process for the rapid production of large amounts of alpha-amylase is also disclosed.

7 Claims, 3 Drawing Sheets

METHOD FOR PRODUCTION OF ALPHA-AMYLASE IN RECOMBINANT BACILLUS

This is a divisional of U.S. patent application Ser. No. 09/684,337, filed Oct. 10 2000, now abandoned, the disclosure of which is incorporated by reference.

The present invention relates to recombinant *Bacillus* strains, and to a process for producing alpha-amylase using such strains.

BACKGROUND OF THE INVENTION

Bacteria belonging to the genus *Bacillus* have attractive properties for the production of industrially important enzymes. They are safe, noninfectious to humans, do not produce toxic substances, and can easily secrete gene products into the culture broth, unlike *E. coli* and yeasts.

Alpha-amylase is one of the industrially most important enzymes and is used in large amounts, for example, in the textile and food industries, for the hydrolysis of starch. The industrial production of alpha-amylase is thus of substantial economic importance.

In the manufacture of alpha-amylase, it is generally known that by fermentation with different types of microorganisms of the genus *Bacillus*, including *Bacillus subtilis* and its variants, alpha-amylase can be obtained in commercially useful amounts. It is particularly advantageous if the fermentation medium itself already contains high concentrations of the active enzyme. There has, therefore, been much to apply new cultivation and processing techniques to obtain the highest possible enzyme concentration in the fermentation medium. For example, Yoneda et al. in Applied And Environmental Microbiology (Vol 39) 274 et seq. (1980); Molecular Cloning And Gene Regulation In Bacilli (Ganesan et al. eds 1982) have described a process using a strain of *B. subtilis* which is employed in industry and has been modified by means of a specific transfer of gene fragments to increase the yield of alpha amylase in the fermentation liquor from 130-150 alpha-amylase units/ml to 25,000 alpha-amylase units/ml, the term "alpha-amylase units" having an art-recognized meaning set out in detail below. This increase represents an improvement by a factor of about 170 in the production of alpha-amylase. Such an increase in productivity is, however, still insufficient for the industrial production of alpha-amylase.

Currently, by virtue of the progress of gene recombination technology and plasmid expression vectors in *B. subtilis*, alpha-amylase genes have been inserted into plasmid expression vectors for over-expression. As host bacteria for producing alpha-amylases of the foreign alpha amylase genes in such gene recombination technology, strains of *B. subtilis* are widely used because their biological characteristics have been sufficiently investigated and further, they have no known pathogenicity and can easily grow in culture media having relatively simple compositions. However, the use of plasmid systems require the addition of antibiotics to the culture medium for maintaining the stability of the plasmid, see, for example, Wei et al., Biotechnology and Bioengineering 33, 1010-1020 (1989). Retention of recombinant cells over prolonged periods in continuous cultures is not possible without continuous applications of antibiotic selection pressure owing to segregational plasmid instability. The use of antibiotics is expensive for industrial scale production. The presence of antibiotics also increases the cost of the down stream processing as the presence of antibiotics in the final product is not acceptable in most food applications.

An important application for phage expression vectors lies in the overexpression of cloned genes for purposes of protein purification. The prophage-based vectors have the advantages of increased stability because of their chromosomal locations and convenient regulation provided by the phage immunity system. Moreover, phage induction, which can be controlled by temperature shift in appropriate mutants, results not only in expression from strong phage promoters but also in an increased copy number through phage DNA replication.

Expression vectors have been developed from the temperature phage $\phi$105, which is present in most of the genetic strains of *B. subtilis*, see Seaman, E et al. 1964, Biochemistry 3, 607-613. Several modifications have been incorporated in the prophage: (i) a mutation rendering the prophage temperature inducible, (ii) the identification of a suitable cloning site within a strongly induced transcription unit, and (iii) a mutation preventing lysis of the host cell. Clearly, for a secreted gene product, it is desirable that the host cell does not lyse so that product can be purified from the cell supernatant. Vectors for high level protein production have been developed recently, mainly by the identification and use of a strong $\phi$105 promoter. $\phi$105MU209 was isolated as a colony exhibiting extremely strong expression of beta-galactosidase amount transformants generated by random insertion of a lacZ reporter gene into a temperature-inducible $\phi$105 prophage, see Errington, J 1986. P. 217-227, in A T Ganesan and J A Hoch (ed.), Bacillus Molecular Genetics and Biotechnology Applications, Academic Press, Inc, Orlando, Fla. The structure of the insertion in $\phi$105MU209 is complex. However, it is clear that the insertion has not only conferred strong inducible expression of lacZ following temperature induction but has also blocked host cell lysis that normally follows phage induction. The lacZ gene lies downstream from the strong dual phage promoters, see Leung, Y C and Errington, J, 1995. Gene 154, 1-6, that can be induced about 100-fold by thermoinduction of the prophage, which carries the cts-52 mutation. To facilitate the expression of other proteins in this system, the lacZ gene and part of the chloramphenicol resistance gene have been replaced with an erythromycin resistance gene. The resulting prophage expression vector was named as $\phi$105MU331, Thornewell, S J et at, 1993, Gene 133, 47-53.

The method of homologous recombination has been used to replace the erythromycin resistance gene with heterologous genes, which are then overexpressed following thermoinduction. This system has been used to produce the secreted *Bacillus cereus* beta-lactamase I, with yields of about 0.5 g/l. The constructions are stable in the absence of selection (before induction), and it seems likely that phage DNA replication and the resultant increase in copy number contribute to the high level of expression.

OBJECTS OF THE INVENTION

It is an object of the present invention to provide a recombinant *Bacillus* strain capable of overexpressing alpha-amylase.

A related object is the provision of a process for producing alpha-amylase utilizing the recombinant Bacillus strain.

A further related object is the provision of a method for hydrolysing starch which employs alpha-amylase from a recombinant *Bacillus* strain.

A more detailed object of this invention is to provide a novel recombinant *Bacillus* prophage strain which is stable even in the absence of antibiotics and is constructed by recombinant DNA technology to possess an enhanced capability to synthesize alpha-amylase in culture typically within a short period of time after heat induction.

It is another object of the present invention to provide a fast process of alpha-amylase synthesis via heat inducible enzyme production and fermentation effected by culturing and heat shocking a novel recombinant Bacillus prophage strain.

SUMMARY OF THE INVENTION

The present invention provides a biologically pure culture of a Bacillus strain comprising an alpha-amylase gene inserted in the *Bacillus* chromosome under transcriptional control of a phage promoter.

PREFERRED EMBODIMENTS

In accomplishing the foregoing objects, there has been provided, in accordance with the present invention, a biologically pure culture of a Bacillus strain, preferably a strain of *Bacillus subtilis*. The strain comprises an alpha-amylase gene inserted in the chromosome of the *Bacillus*. The gene inserted in the chromosome is under transcriptional control of a phage promoter.

The strain over-expresses alpha-amylase. The strain is preferably capable of producing alpha-amylase at culture density ($A_{600nm}$) above 3.0, usually between 3.0 and 5.0. The strain is preferably capable of producing alpha-amylase in an amount of at least about 600,000 alpha amylase units per ml of fermentation medium.

Such yields are remarkably high in comparison to the existing technology for producing alpha-amylase. *Bacillus brevis* 47 was isolated from soil in 1976 and was found to be an excellent producer of proteins in nutrient-rich medium. Under optimal conditions, *B. brevis* can secrete proteins up to mass densities of 30 g/L in nutrient-rich medium and the yield of protein production has been estimated to be as high as 80% on the basis of glucose consumption in synthetic defined media. In 1996, Park et al. [Biotechnology and Bioehgineering, Vol. 49, pp. 36-44 (1996)] observed enhanced alpha-amylase production in recombinant *Bacillus brevis* by fed-batch culture with amino acid control. They used an on-line L-amino acid concentration control system and applied it to the fed-batch culture of a *B. brevis* strain harboring a plasmid containing the alpha-amylase gene. The purpose was to improve production of recombinant alpha-amylase in *B. brevis*. They reported that the maximum recombinant protein (alpha-amylase) level increased from 5,140 U/ml (at the culture time of 27 h) in conventional fed-batch culture to 12,010 U/ml (at a slightly shorter culture time of 24 h) when L-amino acid concentration was controlled at 5 mM using an asparagine- and isoleucine-enriched nitrogen source.

In 1980, Yoneda et al. [Applied and Environmental Microbiology, Jan. 1980, pp. 274-276] have described a process using a strain of *Bacillus subtilis* which is employed in industry and has been modified by means of a specific transfer of gene fragments to increase the yield of alpha-amylase in the fermentation liquor from 130-150 U/ml to 25,000 U/ml. This increase represents an improvement by a factor of about 170 in the production of alpha-amylase. Such an increase in productivity is, however, still insufficient for the industrial production of alpha-amylase.

A big improvement was made in 1986, when a patent was issued for the discovery of the bacterial strain *Bacillus subtilis* DSM 2704 [Inventor: Lompe; Arved, Nienburg, Germany. Patent No.: US04610964. Title: Novel microorganism and its use in a process for the preparation of alpha-amylase]. This strain can produce alpha-amylase in amounts of about 200,000 U/ml (at the culture time between 50 to 70 h).

In a particularly preferred embodiment, the invention resides in a recombinant *B. subtilis* strain designated as *B. subtilis* prophage AB101. This strain is capable of producing alpha-amylase when cultured in a fermentation medium containing an assimilable source of carbon and an assimilable source of nitrogen after heat shock at culture density ($A_{600nm}$) >3.0. The aforementioned strain usually produces alpha-amylase in amounts of at least about 600,000 alpha amylase units per ml of the fermentation medium.

The newly constructed recombinant *Bacillus subtilis* strain AB101 is thus far superior to all known microorganisms of the same species and type in the production of alpha-amylase. With an optimized fermentation process, a large quantity of alpha-amylase is produced only about 6-8 after thermo-induction. The culturing time before heat shock is only about 4-6 h. That means a total culture time of just 10-14 h is be sufficient for obtaining large amount (600,000 U/ml) of alpha-amylase. Therefore, there is a big improvement in both alpha-amylase productivity and production rate. These two parameters are very important for the industrial production of alpha-amylase.

There has also been provided in accordance with the present invention a process for producing alpha-amylase, comprising the steps of culturing and heat induction, in a fermentation medium containing an assimilable carbon source and an assimilable nitrogen source, a recombinant *Bacillus* of this invention. In a preferred embodiment, the fermentation medium comprises a liquid culture medium for the aforementioned strain.

DETAILED DESCRIPTION OF PREFERRED EMBODIMENTS

Figure 1:
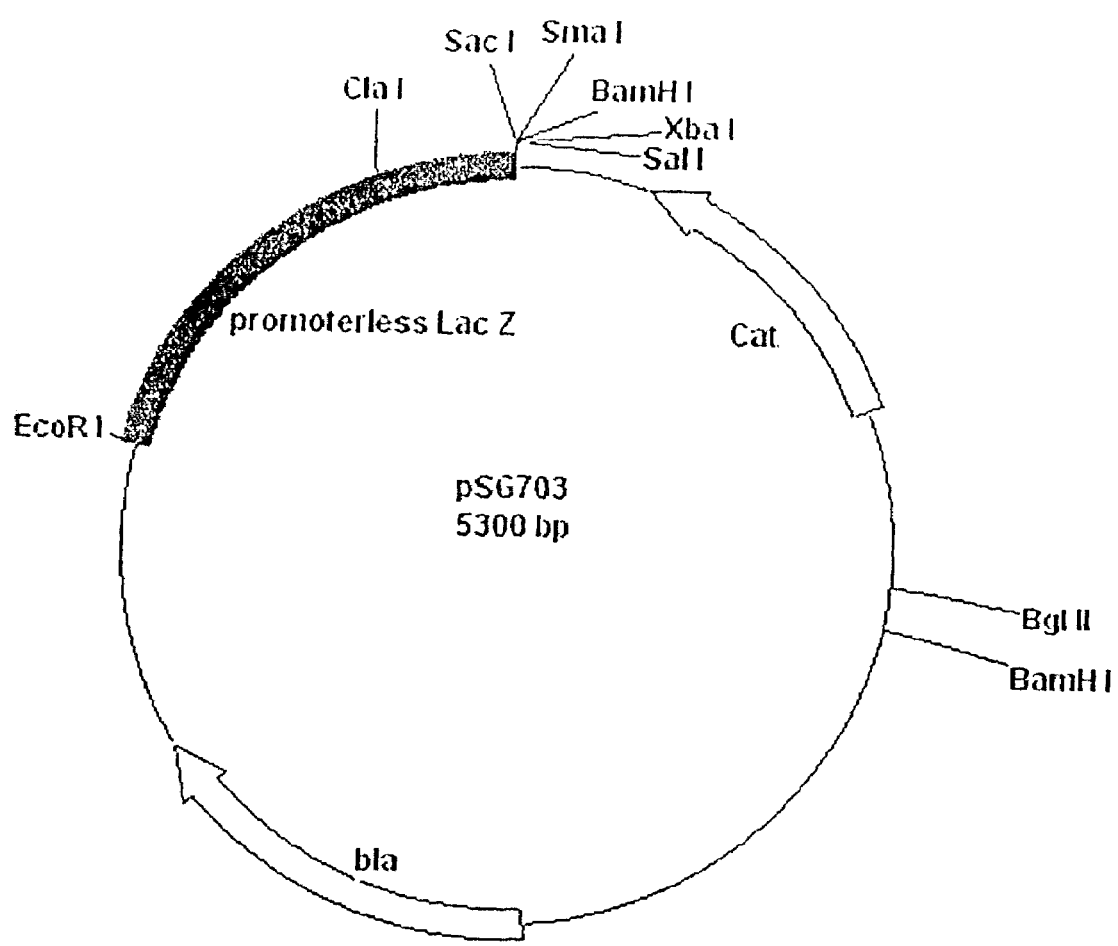
FIG. 1 shows a vector for the insertion of heterologous genes into the *B. subtilis* φ105MU331 prophage. Plasmid pSG703 was constructed as described by Thornewell et al, 1993.

For the high level production of a recombinant protein, the gene has to be inserted at the down-stream of a good promoter, which should have the following properties. First, it has to be strong, resulting in rapid gene transcription, and providing adequate mRNA for the further steps of recombinant protein synthesis. Second, it should be under tight regulation. Recombinant gene expression lays additional metabolism burden to the host cell, and impedes the host cell growth. Therefore, recombinant gene transcription should be occluded in the rapid growth phase, to give rise to maximum cell growth and high level expression of the recombinant gene. Third, it should be controlled by induction using simple and cost effective methods, such as temperature shift.

Because of its potential for secreting large amount of protein and its popularity, *Bacillus subtilis* is regarded as a component workhorse for heterologous protein production. Large amounts of medically and industrially important proteins have been successfully produced from recombinant *B. subtilis*. However, in respect of heterologous gene stability, recombinant systems in which the foreign gene is integrated into the host chromosome are more appreciated.

In accordance with the invention, the alpha-amylase gene is integrated into the chromosome of the *Bacillus* strain using recombinant technology. Furthermore, the inserted gene is under transcriptional control of a phage promoter, preferably the temperate phage $\phi$105. Suitably the prophage has one or more, preferably all, of the following characteristics:

(i) a mutation rendering the prophage temperature inducible;
(ii) a suitable identified cloning site within a strongly induced transcription unit; and
(iii) a mutation preventing lysis of the host cell.

The preferred prophage expression vector is $\phi$ 105MU331.

Thus, a particularly preferred *Bacillus* strain of this invention comprises an alpha-amylase gene at the expression site of the prophage $\phi$105MU331 integrated in the chromosome of the *Bacillus* strain.

The recombinant strain can be modified to produce alpha-amylase enzymes encoded by alpha-amylase genes obtained from prokaryotic and eukaryotic living organisms. The preferred source of the alpha-amylase gene is a *Bacillus amyloliquefaciens* alpha-amylase gene, such as that in plasmid pDLP3. The gene can be suitably incorporated in a cloning vector, such as plasmid pSG703, and thereby give a transformation vehicle such as plasmid pEG 101 for recombination with a competent *Bacillus* strain.

More details are to found in the article Gene 133, 47-53, 1993 which is specifically incorporated by reference.

A particularly preferred strain of this invention is *Bacillus subtilis* strain AB101. The procedure given in the present Examples will always reproducibly yield this strain *Bacillus subtilis* strain AB101.

The use of the phage $\phi$105 to provide transcriptional control is not critical. For example, PBSX is a defective phage and is present in most of the genetic strains of *B. subtilis*. By manipulation of the PBSX prophage of *B. subtilis* 168, another system had been developed. Campbell-type integration introduces a plasmid carrying the gene to be expressed into the PBSX prophage and downstream from a prophage promoter [O'Kane, C. et al. (1986) J. Bacteriol. 168, 973-981]. The prophage carries a mutation, xhi-1479 [Buxton, R. S. (1976) J. Virol. 20, 22-28], that allows thermoinduction of prophage development, and the plasmid insertion blocks lysis of the host cell because the genes needed lie downstream from the same promoter [Wood, H. E. et al., (1990) J. Bacteriol. 172, 2667-2674]. The construction is relatively stable and is maintained in single copy during the growth phase. Transcription and DNA amplification are activated by thermoinduction.

In another variation, the recombinant strain can be modified to produce alpha-amylase enzymes encoded by artificially synthesised or mutated alpha-amylase genes.

A particular advantage of the preferred recombinant strains of the present invention is that they are stable without adding antibiotics, as the alpha-amylase is induced by a brief period of heat shock and no expensive chemicals such as IPTG are required for starting gene expression. Other mutants created by recombinant DNA technology can be used to advantage in the alpha-amylase production process of the present invention, especially if they produce at least 550,000 U/ml, preferably at least 600,000 U/ml, of alpha-amylase during fermentation.

Fermentation can be controlled and maintained in accordance with presently available techniques. Similarly, the appropriate nutrient cultures are prepared by known methods. Suitable nutrients ordinarily contain assimilable carbon sources, assimilable nitrogen sources, and other conventional nutritive and auxiliary substances which favour or are necessary for the growth of *Bacillus* microorganisms. Various sugars and sugar-containing substances are suitable sources of carbon, and the sugars may be present in different stages of polymerisation. The following sugars are exemplary of those suitable for use in the process of the present invention: starch, dextrin, cane sugar, lactose, maltose, fructose, glucose. As sources of nitrogen, inorganic and organic nitrogen compounds may be used, both individually and in combination. Illustrative examples of suitable nitrogen sources include protein-containing substances, such as peptone from soy beans, meat and casein, gelatins, yeast protein or yeast extract, wastes from the processing of meat and animal bodies, and ammonium salts. It is also advantageous that the nutrient media include inorganic salts, in particular alkaline and alkali earth metal salts and phosphates, together with trace elements, such as Fe, Mg, Mn, Co, and Ni.

Fermentation is typically carried out at pH values between about 5 and 9, preferably between about 6 and 8, and a temperature of 33 to 45° C., preferably 37° C. The duration of fermentation before heat induction is between about 3 and about 8 hours, preferably between 4 and 6 hours. Heat shock is usually performed at a temperature of 50 to 53° C. for 5 to 15 minutes when the culture density ($A_{600nm}$) is between 3.0 and 6.0 preferably between 4.0 and 5.0.

In the preferred process of this invention, the fermentation is a rapid and efficient process, in terms of alpha-amylase activity units generated per fermentation hour.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from the detailed description.

EXAMPLES OF THE INVENTION

Isolation of Plasmid pSG703

Plasmid pSG703 (FIG. 1) was isolated from the *E. coli* DH5α clone carrying the pSG703 (Thornewell, S J et al, 1993. Gene 133, 47-53) by using the Wizard Plus Minipreps DNA Purification System (Promega Co). This plasmid was used as the vector for the subcloning of the *Bacillus amyloliquefaciens* alpha-amylase gene.

Isolation of Plasmid pDLP3

Plasmid pDLP3, carrying the *B. amyloliquefaciens* alpha-amylase gene, was isolated from the *E. coli* XL1-Blue clone carrying the pDLP3 (Steyn A J and Prestorius I S 1991, Gene 100, 85-93) by using the Wizard Plus Minipreps DNA Purification System (Promega Co).

Construction of Plasmid pEG101 from pSG703 and pDLP3

The plasmid pSG703, isolated using the above protocol, was treated with the restriction endonucleases SmaI and ClaI in a reaction medium [composed of 25 mM Tris-acetate (pH 7.8), 0.1 M potassium acetate, 10 mM magnesium acetate and 1 mM DTT (multi-core buffer)] at 37 C. for 1.5 h. After completion of the treatment, the reaction mixture was subjected to agarose gel electrophoresis, and a DNA fragment having a size of about 5 kb was recovered from the gel by using the Qiaex II Gel Extraction Kit (Qiagen Co).

Separately, the plasmid pDLP3 was treated with the restriction endonucleases PvuII, ClaI and PstI in a reaction medium [composed of 6 mM Tris-HCl (pH 7.5), 50 mM CaCl, 6 mM $MgCl_2$ and 1 mM DTT (Buffer B)] at 37 C. for 1.5 h. After completion of the treatment, the reaction mixture was subjected to agarose gel electrophoresis, and a DNA fragment having a size of about 2.1 kb was recovered from the gel. This DNA fragment, containing the *B. amyloliquefaciens* alpha-amylase gene, was joined by using T4 DNA ligase to the above 5 kb DNA fragment. The plasmid pEG101 was thus constructed. Further, with the use of the plasmid pEG101, transformation of *E. coli* (DH5α) was carried out according to the conventional calcium method (Sambrook et al, 1989).

Construction of the Novel Recombinant *B. subtilis* Prophage Strain AB101

Figure 2:
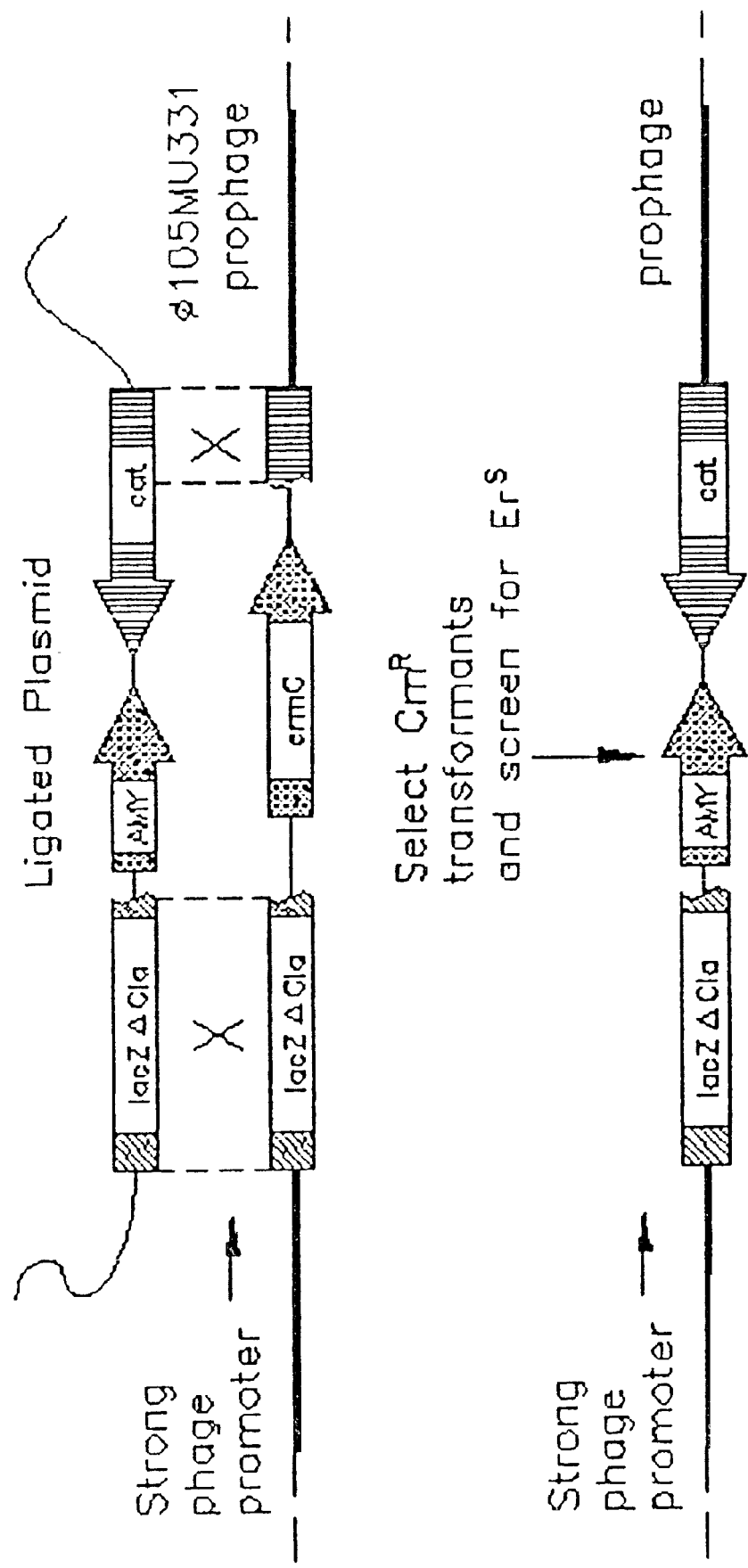
FIG. 2 is a schematic drawing of the construction of a *B. subtilis* prophage allowing expression of alpha-amylase. Plasmid pEG101 (shown linearised, as it was digested with BglII before transformation) was transformed into the *B. subtilis* strain 1A304 (φ105MU331) with selection for the $Cm^R$ marker, and the transformants were screened for an $Er^S$ phenotype. Such transformants should have arisen from a double-crossover event, as shown, placing transcription of the alpha-amylase gene (amy) under the control of the strong phage promoters. The thick lines represent the prophage genome; broken lines the *B. subtilis* chromosome, and thin lines plasmid DNA. The genes are shown as shaded arrows pointing in the direction of transcription and translation. Regions of homology are bounded by broken vertical lines and homologous recombinant events by 'X'.

The plasmid pEG101 was extracted and purified from the clone carrying the pEG101 by using the Wizard Plus Minipreps DNA Purification System (Promega Co). The plasmid pEG101 was then treated with the endonuclease BglII to linearise the plasmid. In the linearised pEG101, the alpha-amylase gene was flanked by the truncated lacZ gene fragment and the cat gene (FIG. 2). This linearised DNA (1 µg) was used to transform competent *B. subtilis* 1A304 (φ105MU331) according to the known method (Anagnostopoulos C and Spizizen J, 1961, J Bacteriol 81, 741-746).

Fifty four chloramphenicol resistant ($Cm^R$) colonies were obtained from plating 600 µl of the transformed cells on an agar plate containing chloramphenicol (5 µg/ml). These colonies were streaked onto an agar plate containing erythromycin (5 µg/ml) and 3 of these colonies did not grow, indicating that they were erythromycin sensitive ($Er^s$). One such chloramphenicol resistant but erythromycin sensitive colony was thus isolated and named as AB101. In the chromosome of this newly constructed prophage strain, the erythromycin resistance gene was replaced by the alpha-amylase gene by a double crossover event in a process of homologous recombination. The truncated lacZ gene fragment and cat gene provided the homologous sequences for the recombination. In this way, the alpha-amylase gene was targeted to the expression site in the prophage DNA of *B. subtilis* 1A304 (φ105MU331) and the alpha-amylase gene was put under the control of the strong thermoinducible promoter.

Production of Alpha-amylase

Figure 3:
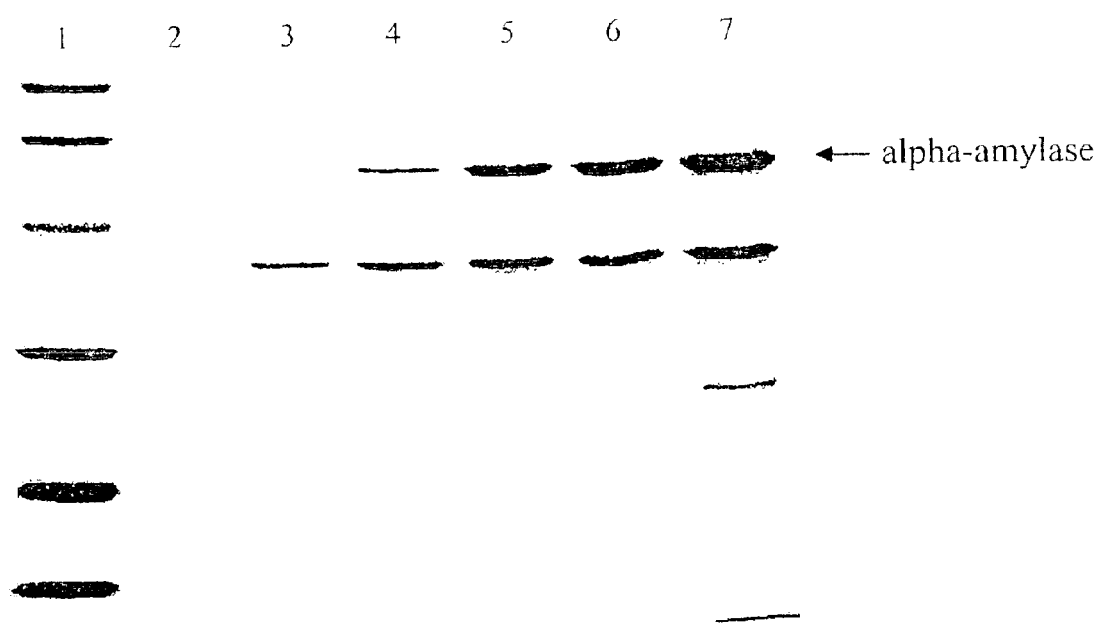
FIG. 3 provides a time-course for the production and secretion of alpha-amylase by the recombinant prophage strain AB101 following thermoinduction. The strain was grown and induced as described. Samples (10 μl) of culture supernatant taken 0 h, 1 h, 3 h, 5 h, 7 h and 9 h after induction (lanes 2-7, respectively) were loaded directly onto a 0.1% SDS-12.5% polyacrylamide gel and subjected to electrophoresis. The proteins were stained with Coomassie blue. Lane 1 contains size markers (kDa), with their molecular weights indicated on the left margin.

The newly constructed recombinant *B. subtilis* prophage strain is far superior to all known microorganisms of the same species and type in the production of alpha-amylase. Large quantity of alpha-amylase is produced only 6-8 hours after heat shock (FIG. 3). The culturing time before heat shock is only about 4-6 hours. That means a total time of just about 10-14 hours would be sufficient for obtaining large amount of alpha-amylase. To our knowledge, there are no previous reports of such large yields of a secreted alpha-amylase being obtained over such a short period of expression using a *B. subtilis* expression system. The concentration of alpha-amylase in a fermentation media where AB101 is cultivated, in accordance with the present invention, is consistently over 600,000 U/ml, and can exceed 650,000 U/ml where an alpha-amylase unit (U) corresponds to a 2.5% reduction of the iodine storage colour complex prepared by the method of Park et al., described in greater detail below.

Production of Alpha-amylase

Batch and fed-batch fermentation in a 2-liter fermentor was performed using the following method:

Medium A

Medium A contained 400 g/l glucose and 5 g/l $MgSO_4.7H_2O$

Medium B

Medium B contained 100 g/l tryptone, 15 g/l $K_2HPO_4$ and 7.5 g/l $KH_2PO_4$

Fermentation Technique

The medium composition for batch culture was the same as that for shake flask cultivation. Heat shock was carried out at late exponential growth phase, culture density ($A_{600nm}$) between 4.0 and 5.0. The fermentation liquid culture was heated up to 50° C. and then cooled down to 37° C. with the internal temperature control system of the fermentor (Biostat B model, B. Braun Biotech International). The dissolved oxygen concentration was controlled at 40% air saturation with the adjustment of stirring speed. The base medium for fed-batch fermentation was similar to that of the batch fermentation, except that the glucose concentration was reduced to 1 g/l. Medium A and medium B were used as the feeding media. They were autoclaved separately and mixed with equal volumes before feeding. The medium feeding rate was controlled with the pH-stat control strategy [Suzuki et al., 1987; Jeong et al., 1999].

To determine alpha-amylase activity, the method of Park et al. was used, see Biotechnology and Bioengineering 49, 36-44 (1996). High purity soluble starch (Sigma Chemical Co, Catalog No. S9765) was used as the enzyme substrate. All other reagents were of standard, analytical grade quality.

Soluble starch solution (0.2%)

2% soluble starch solution was prepared by measuring 2.000 g of soluble starch with a balance. This powder was added to 10 ml distilled water and stirred. This mixture was then added slowly into 80 ml boiling distilled water and boiled until it was a clear solution. The final volume was adjusted to 100 ml with distilled water after the solution was cooled down. It was necessary to prepare this solution fresh daily. The 0.2% solution was prepared by diluting this concentration stock solution with distilled water.

Reagent A

A solution containing 0.2% iodine and 2% potassium iodide was prepared daily from a five times concentration stock solution by dilution with water.

Analytical Technique

50 µl of 0.5 M glycine-NaOH buffer at pH 9.0 and 50 µl of enzyme-containing solution, optionally diluted with a potassium acetate solution, were mixed with 100 µl of the soluble starch solution (0.2%) and incubated for 10 min in a water bath at 50 C.

The reaction was stopped by the addition of 200 µl of 1.5 N acetic acid. The 200 µl of Reagent A and 3.4 ml of distilled water were added to the mixture, and the absorbance was measured at 690 nm with light path of 10 mm. One amylase unit (U) corresponds to a 2.5% reduction of the iodine starch colour complex thus formed. In the range of 1 to approximately 5 amylase units, the calibrating curve was linear.

Sodium dodecyl sulfate-poylacrylamide gel electrophoresis (SDS-PAGE) was carried out as described in the standard protocol [Sambrook et al, 1989].

SDS-PAGE Sample Loading Buffer

This loading buffer contained 2% SDS, 5% beta-mercaptoethanol, 10% glycerol and 0.002% bromophenol blue.

Analytical Technique

The separating gel concentration used was 12.5%. The culture supernatant (10 µl) was mixed with equal volume of the SDS-PAGE sample loading buffer. The mixture was incubated in boiling water for 5 min, cooled down on ice and loaded onto the gel for electrophoresis.

STATEMENT OF DEPOSIT OF BIOLOGICAL MATERIAL

A deposit of biological material *Bacillus subtilis* AB 101 was made under the Budapest Treaty on Nov. 11, 2008 with the following depository:

China General Microbiological Culture Collection Center (CGMCC), Institute of Microbiology, Chinese Academy of Sciences, Datun Road, Chaoyang District, Beijing 100101, China.

Viability was established on Nov. 17, 2008. The accession number of the deposit is CGMCC No. 2740.

OTHER REFERENCES

Sambrook J, Fritsch, E F and Maniatis T (1989) Molecular Cloning, A Laboratory Manual, second edition, Cold Spring Harbor Laboratory Press, New York.

Yoneda et al., Applied and Environmental Microbiology, Jan. 1980, pp 274-276.

What is claimed is:

1. A process for production of alpha-a mylase from *Bacillus subtilis* strain AB101, deposit accession No. CGMCC No. 2740 comprising:
   a) culturing the *Bacillus subtilis* strain AB101 under batch fermentation conditions at a temperature of 33-45° C. in a medium comprising assimilable sources of carbon and nitrogen, phosphate, and salts of trace elements, where said medium has a pH of about 5-9 and a dissolved oxygen concentration of 5-40% of air saturation;
   b) performing a fed-batch step, wherein the concentration of the assimilable carbon source in the medium is kept in a range from 0.1 g/l to 1 g/l while maintaining continued growth of the cells, and the dissolved oxygen concentration is adjusted to 5to 40% by passing air into the fermentation broth, which comprises
      i) inducing the promoter by a heat shock at a temperature of 50 to 53° C. for 5 to 15 minutes when the culture density ($A_{600nm}$) is greater than 3.0, followed by cooling to 37° C. thereby initiating the production of the alpha-amylase, and
      ii) continuously feeding in assimilable sources of carbon and nitrogen, phosphate, and salts of trace elements; and
   c) removing the *Bacillus subtilis* strain AB101 from the medium;
   wherein the *Bacillus subtilis* strain AB101 produces alpha-amylase with a productivity of over 600,000 alpha-amylase units per mL in a 10-14 hour period.

2. The process of claim 1, wherein the inducing the promoter by a heat shock is carried out at a culture density ($A_{600\ mm}$) between 4.0 and 5.0, at 50° C.; the dissolved oxygen concentration is 40%; and the glucose concentration is 1g/l.

3. The process of claim 1, wherein the *Bacillus subtilis* strain AB101, deposit accession No. CGMCC No. 2740, produces alpha-amylase having a productivity of over 650,000 alpha-amylase units per mL in a 10-14 hour period.

4. The process of claim 1, where said medium has a pH of from about 6 to about 8.

5. The process of claim 1, wherein said saits of trace elements are selected from the group consisting salts of Fe, Mg, Mn, Co, and Ni.

6. The process of claim 1, wherein said assimilable source of nitrogen is selected from the group consisting of soy bean peptone, meat, casein, gelatins, yeast protein, yeast extract, wastes from the processing of meat and animal bodies, and ammonium salts.

7. The process of claim 1, wherein said assimilable source of carbon is selected from the group consisting of starch, dextrin, cane sugar, lactose, maltose, fructose, and glucose.

* * * * *